United States Patent [19]
Braun et al.

[11] Patent Number: 5,532,411
[45] Date of Patent: Jul. 2, 1996

[54] PRODUCTION OF CARBOXYLIC ACID HALIDES AND CARBOXYLATE SALTS

[75] Inventors: Max Braun, Wedemark; Werner Rudolph, Hanover; Stefan Palsherm, Barsinghausen; Kerstin Eichholz, Langenhagen, all of Germany

[73] Assignee: Solvay Fluor und Derivate GmbH, Hanover, Germany

[21] Appl. No.: 233,624

[22] Filed: Apr. 26, 1994

[30] Foreign Application Priority Data

Apr. 27, 1993 [DE] Germany .......................... 43 13 793.8

[51] Int. Cl.$^6$ ........................ C07C 51/58; C07C 69/02
[52] U.S. Cl. .......................... 562/861; 560/231
[58] Field of Search .............. 562/861; 560/231

[56] References Cited

U.S. PATENT DOCUMENTS

| | | | |
|---|---|---|---|
| 2,647,933 | 8/1953 | Zerte et al. | 562/861 |
| 2,704,776 | 3/1955 | Zerte et al. | 562/861 |
| 4,382,897 | 5/1983 | Rudolph et al. | 260/544 X |
| 4,649,216 | 3/1987 | Rule | 562/406 |

FOREIGN PATENT DOCUMENTS

| | | |
|---|---|---|
| 002989 | 7/1979 | European Pat. Off. . |
| 209157 | 1/1987 | European Pat. Off. . |
| 236348 | 9/1987 | European Pat. Off. . |
| 57-7438 | 4/1982 | Japan . |
| 313549 | 6/1956 | Switzerland . |
| 1694567 | 9/1930 | U.S.S.R. . |
| WO81/01406 | 5/1981 | WIPO . |

OTHER PUBLICATIONS

Helinski et al., *Phosphorus, Sulfur and Silicon*, vol. 54, pp. 225–225 (1990).
Dauben et al., *J. Am. Chem. Soc.*, vol. 776, pp. 4618–4619 (1954).
Olah et al., *J. Org. Chem.*, vol. 26, pp. 237–238 (1961).
Chemical Abstracts 1943:1990-4.
Haszeldine, *J. Chem. Soc.*, 1951: pp. 584–587.
Dauben et al., "Isomerization of Isospirostans . . .", vol. 76, pp. 4618–4619 (Sep. 20, 1954).
Olah et al., "Organic Fluorine Compounds . . .", vol. 27, pp. 237–238 (Jan. 1961).
Olah et al., *J. Chem. Soc.*, 96:(3), 925–7 (1974).
Vedova et al., *J. Raman Spectroscopy*, 20:135–140 (1989).
Chemical Abstracts, 114:6668t (1991).

*Primary Examiner*—Paul J. Killos
*Attorney, Agent, or Firm*—Evenson, McKeown, Edwards & Lenahan

[57] ABSTRACT

A process for preparing carboxylic acid halides and carboxylate salts by reacting metal or "onium" halides with carboxylic anhydrides, which process is very suitable for working-up anhydrous, spent catalyst preparations. The resulting carboxylic acid halide or carboxylate salt can be used as an acylating reagent or alkylating reagent, and metal halide or "onium" halide liberated during this can be reacted anew with carboxylic anhydride and regenerated, thereby making it possible to effect a hydrolysis-free alkylation or acylation without forming salt-type waste products. If the mixture of carboxylic acid halide and carboxylate salt is allowed to react with an alcohol, preferably in situ, the resulting ester can be isolated without hydrolysis.

27 Claims, No Drawings

PRODUCTION OF CARBOXYLIC ACID HALIDES AND CARBOXYLATE SALTS

BACKGROUND OF THE INVENTION

This invention relates to a process for preparing carboxylic acid halides and carboxylate salts.

Carboxylic acid halides, for example trifluoroacetyl chloride, trifluoroacetyl bromide or trifluoroacetyl iodide, are valuable intermediates in chemical synthesis, for example in the preparation of herbicides, surfactants and pharmaceuticals. For example, trifluoroacetyl chloride is a polymerization initiator for tetrafluoroethylene.

Carboxylic acid salts are also valuable intermediates in synthesis. Thus, halogen-substituted aromatic compounds can be converted to the corresponding trifluoromethylated aromatic compound using sodium trifluoroacetate with elimination of sodium chloride and decarboxylation.

One industrial process for preparing trifluoroacetyl chloride is described in U.S. Pat. No. 4,382,897, in which 1,1,1,-trifluoro-2,2,2,-trichloroethane is reacted with sulfur trioxide in the presence of mercury salts and, additionally, boron halide and/or halosulfonic acid. The resulting $CF_3C(O)Cl$ can be converted, for example by means of alcohols, to esters of trifluoroacetic acid. Carboxylic acid bromides and carboxylic acid iodides can be produced from the corresponding carboxylic acid chlorides by using anhydrous hydrogen bromide or hydrogen iodide, see R. N. Haszeldine, *J. Chem. Soc.* 1951, pages 584 to 587. Another industrial process for preparing trifluoroacetyl bromide and trifluoroacetyl iodide is disclosed in Japanese Patent Application No. JP-A 2/262 530. In this process the corresponding acetyl fluoride is reacted with lithium bromide or lithium iodide. In addition, it is known to prepare trifluoroacetyl halides by reacting trifluoroacetic acid anhydride with phosphoric acid chlorides or phosphinic acid chlorides. A mixed anhydride of phosphonic acid or phosphinic acid and trifluoroacetic acid is formed as a by-product, which is industrially worthless. This process is described by J. Helinski et al. in *Phosphorus Sulfur Silicon Relat. Chem.* 54 (1990), pages 225 and 226. Thus, the known processes, especially for preparing carboxylic acid halides, are technically difficult to carry out, or they form unwanted waste products.

SUMMARY OF THE INVENTION

It is the object of the present invention to provide a process particularly for preparing carboxylic acid halides.

Another object of the invention is to provide a process for preparing carboxylic acid halides which is technically easy to carry out.

A further object of the invention is to provide a process for preparing carboxylic acid halides which does not produce large amounts of undesired waste products.

Yet another object of the invention is to provide a process for simultaneously preparing carboxylic acid halides and carboxylate salts.

These and other objects of the invention are achieved by providing a process for simultaneously preparing a carboxylic acid halide and a carboxylate salt formed from carboxylate anions and 1/n cations $M^{n+}$ selected from the group consisting of metal cations and "onium" cations, wherein n+ represents the positive charge of the cation, said process comprising reacting a carboxylic anhydride with a compound corresponding to the formula $M^{n+}(Hal^-)_n$, wherein $Hal^-$ represents chloride, bromide or iodide.

DETAILED DESCRIPTION OF PREFERRED EMBODIMENTS

In accordance with the invention carboxylic acid halides and carboxylate salts composed of carboxylate anions and 1/n $M^{n+}$ cations, where $M^{n+}$ is the cation of a metal or an "onium" cation and n+ represents the positive charge of the cation, are simultaneously produced by reacting a carboxylic anhydride with a compound $M^{n+}(Hal^-)_n$, where $Hal^-$ represents chloride, bromide or iodide. As used herein, the term "carboxylic acid halide" refers to a carboxylic acid chloride, bromide or iodide. Carboxylic acid chlorides are preferred.

Advantageously, approximately n equivalents of the carboxylic anhydride, or a slight excess, are used. Naturally, it is also possible, with reduced yield, to use the carboxylic anhydride in less than equivalent amounts. Good results are obtained when 0.95 n to 1.05 n equivalents of the carboxylic anhydride are used. For example, it is possible to react 1 mole of $AlCl_3$ (n=3) with 3 moles of acetic acid anhydride to give acetyl chloride and aluminum acetate.

Preferred metal cations are those of groups I, II and III of the periodic table, particularly sodium, potassium and aluminum. In the present invention "n" is an integer, preferably 1, 2 or 3.

As used herein, the term "onium" cation refers to a molecule with a positively charged nitrogen atom.

An advantageous property of the process according to the invention is that only valuable products are formed without formation of waste products.

In accordance with a preferred embodiment, the starting material $M^{n+}(Hal^-)_n$ is used in the form of anhydrous waste products, as formed in chemical or physical processes. "Onium" halides serve for example as catalysts or phase-transfer catalysts, for example in preparing organic carbonates from organic acids, carbon monoxide and oxygen and in the presence of further catalytically active substances. "Onium" halides are also formed, for example, in base-catalyzed reactions of C—H acidic compounds, e.g. malonates, with carboxylic acid halides. Metal halides, e.g. sodium chloride, contaminated with organic material are a waste product in the reaction of sodium salts of carboxylic acids with, for example, halogenated aromatics to give alkylated aromatics. Such waste products or spent catalysts can be converted to valuable products by the process according to the invention.

According to a variant of the process according to the invention, the carboxylic acid halide and the carboxylate salt are not isolated. In this variant the reaction mixture containing the carboxylic acid halide and carboxylate salt is reacted further to, for example, carboxylic acid esters without isolating the carboxylic acid halide and/or the carboxylate salt (see below).

According to another variant of the process according to the invention, the reaction mixture is separated into carboxylic acid halide and carboxylate salt. This is very readily achieved by evaporating the volatile carboxylic acid halide, preferably in vacuo. The separated products can be used as intermediates in chemical reactions or as catalysts.

From the foregoing it can be seen that the reaction products obtained from the reaction of metal halides or "onium" halides with carboxylic anhydrides can be used in processes in which metal halides or "onium" halides are liberated again, for example in acylation processes, alkylation processes, esterification or in preparing ketones. The liberated halide can be reacted anew with carboxylic anhydride and regenerated again. In this manner it is possible to carry out an acylation, alkylation, esterification or preparation of ketones without forming waste salts and or needing a hydrolysis step. This embodiment of the process according to the invention is particularly preferred and characterized by the use of the carboxylic acid halide and/or carboxylate salt in reactions where $M^{n+}(Hal^-)_n$ is liberated anew and reacted again with carboxylic anhydride and regenerated. In this manner a continuous or semi-continuous procedure is possible without salts being formed. In addition, a hydrolysis-free procedure is possible.

In principle the process according to the invention is suitable for reacting any halides with any carboxylic anhydrides. In some cases, however, in order to increase the rate of the reaction it is desirable to use an aprotic solvent for the anhydride, for example a hydrocarbon or a monomeric, oligomeric or polymeric ether, or an aprotic solvent for the halide, for example one of the known polar solvents such as nitriles, lactams, ethers, etc. If desired, the rate of reaction can also be increased by the addition of phase-transfer catalysts such as crown ethers.

Very good results are obtained when carboxylic anhydrides of carboxylic acids with 2 to 4 carbon atoms are used. It is particularly advantageous to use carboxylic anhydrides of carboxylic acids with 2 to 4 carbon atoms which are substituted with 1 to 7 halogen atoms, preferably 1 to 7 fluorine atoms, such as, for example, trifluoroacetic anhydride.

Sodium halide or potassium halide or an "onium" halide of nitrogen is preferably used as the halide. Halide preferably represents chlorine, bromine and iodine, particularly chlorine and bromine. Especially good results with surprisingly high yields are obtained when "onium" halide is used in the process according to the invention. Thus, $M^{n+}$ preferably represents an "onium" cation of nitrogen corresponding to the formula $R^1R^2R^3R^4N^+$, in which $R^1$, $R^2$, $R^3$ and $R^4$ are independently selected from hydrogen, alkyl with 1 to 20 carbon atoms, aryl or aralkyl, or in which $R^1$ and $R^2$, or in which $R^3$ and $R^4$, or in which $R^1$, $R^2$ and $R^3$, or in which $R^1$, $R^2$, $R^3$ and $R^4$, where appropriate with inclusion of the nitrogen atom, form saturated or unsaturated ring systems, in particular heteroaromatic compounds. Aryl here represents particularly phenyl and phenyl substituted by 1 or more halogen atoms and/or substituted by 1 or more C1-C2-alkyl groups. Salts in which $M^{n+}$ represents ammonium, piperidinium, pyridinium or $R^{1'}R^{2'}R^{3'}R^{4'}N^+$, in which $R^{1'}$, $R^{2'}$, $R^{3'}$ and $R^{4'}$ are, independently of each other, hydrogen, alkyl with 1 to 15 carbon atoms or benzyl are particularly suitable. Good examples which may be mentioned include pyridinium hydrohalides, anilinium hydrohalides, piperidinium hydrohalides, benzyltriethylammonium hydrohalides and triethylammonium hydrohalides, preferably the chlorides and bromides, particularly the chlorides.

In a particularly preferred variant of the invention, the mixture of carboxylic acid halide and carboxylate salt is reacted with an alcohol with the formation of a carboxylic acid ester, during or after the preparation of the mixture. Many esters of carboxylic acids are used as such industrially. Acetic acid esters and other carboxylic acid esters serve, for example, as solvents or detergents. Other esters, e.g. of succinic acid, are used in aromatization. Ethyl trifluoroacetate, for example, is a solvent for the chlorination of paraffins or the polymerization of olefin oxides. Many carboxylic acid esters are also intermediates in chemical synthesis. Methyl trifluoroacetate and 1,1,1-trifluoroethyl trifluoroacetate yield trifluoroethanol after hydrogenation. Trifluoroethanol is used as a solvent and as an intermediate, for example in the preparation of the solvent and anaesthetic isoflurane. Esters of trifluoroacetic acid also serve for the introduction and preparation of biologically active compounds which contain $CF_3$ groups. For example, N-acylation with methyl trifluoroacetate can be used to produce peptides with hormonal activity. Ethyl trifluoroacetate reacts with camphor derivatives to yield shift reagents for NMR analysis. The trifluoromethylphenyl ester yields, after a Fries migration with aluminum chloride, the corresponding trifluoroacetylated phenol, which is a synthetic building block for pharmaceuticals. Many other uses of esters are known to those skilled in the art, for example use in preparing pharmaceuticals, photosensitizers and dyes.

The preparation of carboxylic acid esters is normally carried out by reacting the corresponding alcohols with the carboxylic acids under acid catalysis. The resulting water of reaction has to be removed to shift the equilibrium of the reaction. In the case of fluorinated derivatives this can lead to difficulties because of the preferred binding of water (to the carbonyl functions as hydrates). It is also already known that carboxylic acid esters can be produced from carboxylic acid chlorides and alcohols with base catalysis. However, hydrolytic work-up is necessary, and in addition waste salts are formed, for example pyridine hydrochloride, which have to be disposed of. The reaction of carboxylic acid halides with alcohols proceeds at a reduced rate of reaction without base catalysis.

The invention is based on the knowledge that the resulting product mixture, which contains carboxylic acid halide and carboxylate salt, yields carboxylic acid esters with alcohols. The carboxylate salt surprisingly shows catalytic activity.

Naturally, it is possible first to isolate the carboxylic acid halide and carboxylate salt separately and then react them in the desired amounts with alcohol.

It is also possible, but not required, to add acid, e.g. a carboxylic acid. Preferably acid is not added, particularly in the case of in situ esterification.

The preferred starting materials for preparing esters are carboxylic acid chlorides. Preferably, an "onium" salt of the carboxylic acid is used as catalyst.

The variant of the process according to the invention can in principle be used for preparing any esters of any carboxylic acids with any alcohols. A preferred embodiment of the variant comprises using a carboxylic acid chloride of the formula $R^aC(O)Cl$ (I), in which $R^a$ is alkyl with 1 to 6 carbon atoms; alkyl with 1 to 6 carbon atoms substituted by at least 1 halogen atom; phenyl; tolyl; phenyl or tolyl substituted by at least 1 halogen atom.

In addition, it is preferred to use an alcohol of the formula $R^bOH$ (II) in which $R^b$ is alkyl or alkenyl with 1 to 8 carbon atoms, alkyl or alkenyl with 1 to 8 carbon atoms substituted by at least 1 halogen atom; phenyl; tolyl; benzyl; phenyl, tolyl or benzyl substituted by at least 1 halogen atom and/or at least a nitro group.

It is very particularly preferred when $R^a$ is alkyl with 1 to 4 carbon atoms substituted with at least 1 fluorine atom and $R^b$ is alkyl or alkenyl with 1 to 4 carbon atoms; alkyl or alkenyl with 1 to 4 carbon atoms substituted by at least 1 halogen atom; phenyl; phenyl substituted by at least 1 halogen atom and/or at least one nitro group, especially perfluoromethyl, perfluoroethyl or perfluoropropyl. Particularly preferably, $R^b$ is alkyl or alkenyl with 1 to 3 carbon atoms; alkyl or alkenyl with 1 to 3 carbon atoms substituted by at least 1 fluorine atom; phenyl; phenyl substituted by at least 1 fluorine atom and/or at least one nitro group. Alkenyl, of course, denotes an organic group with at least two carbon atoms.

The process variant is particularly well suited for preparing esters of acetic acid which is substituted by one or more fluorine atoms. For example, phenyl trifluoroacetate can be prepared by the process according to the invention. The process according to the invention is particularly well suited for preparing esters of trifluoroacetic acid or chlorodifluoroacetic acid with 1,1,1-trifluoroethanol, pentafluoropropanol, methanol, ethanol, isopropanol, 4-nitrophenol, pentafluorophenol and allyl alcohol.

The molar ratio between carboxylic acid halide and alcohol is advantageously above 0.9. The alcohol can also be used in large excess and serve as a solvent, particularly when it is an alcohol substituted by electron-withdrawing groups such as fluorine atoms. Advantageously, the molar ratio between the alcohol and the carboxylic acid halide lies between 0.9:1 and 5:1.

The temperature at which the reaction is carried out lies between ambient temperature (about 20° C.) up to the boiling point of the mixture, for example up to 100° C. The process is carried out under ambient pressure (about 1 bar absolute) or optionally at elevated pressure, for example up to 5 bar absolute.

The alkali metal salt or "onium" salt can be present in catalytic or molar amounts. Advantageously, the molar ratio between acid halide and the carboxylic acid salt lies in the range from 1:1 to 20,000:1.

In accordance with a particularly preferred embodiment of the invention, the acid chloride or the acid bromide and the alkali metal or "onium salt" of the carboxylic acid are produced in situ. For this purpose, the corresponding alkali metal halide or "onium" halide, preferably the chloride or bromide, particularly the chloride, is reacted with the anhydride of the carboxylic acid to be used. In this reaction the corresponding acid halide and the corresponding salt form from the anhydride of the carboxylic acid. Spent halide catalysts can be used in this embodiment as the alkali metal halide or "onium" halide, and can be converted in this manner into valuable products.

The process according to the invention has many advantages. For example it works at ambient temperature, although, if desired, the temperature can be raised to, for example, 60° C. or higher. In addition the process according to the invention can be used to produce special acid halides which are difficult to obtain by other processes. In addition, salts which are produced as waste in industrial processes can be converted into valuable products. It is particularly advantageous to use of the process according to the invention when salts are converted to carboxylic acid halides and carboxylic acid salts, which when further processed produce salts again, which can be regenerated anew in the process according to the invention. This procedure makes it possible for the first time to carry out a multiplicity of reactions in such a way that no salt waste is produced and/or no hydrolytic work-up is necessary.

The variant of the invention with esterification has the advantage that carboxylic acid esters can be produced in a technically simple way without hydrolytic work-up. In addition, with most esters, no waste products such as pyridine hydrochloride are produced.

The following examples are intended to illustrate the invention in further detail without limiting its scope.

EXAMPLE 1

Preparation of trifluoroacetyl chloride and pyridinium trifluoroacetate by reaction of pyridinium hydrochloride with trifluoroacetic anhydride.

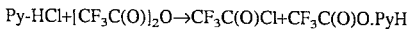

Py.HCl+[CF$_3$C(O)]$_2$O→CF$_3$C(O)Cl+CF$_3$C(O)O.PyH

With exclusion of moisture (N$_2$ atmosphere), 26.17 g (0.226 mole) of pyridinium hydrochloride were taken up in 25 ml of trifluoroacetic acid, and 61.84 (0.227 mole) of trifluoroacetic acid anhydride were continuously added dropwise with stirring over one hour at room temperature. Immediately after the addition of a few drops of trifluoroacetic anhydride, vigorous evolution of gas was observed in the reaction flask. The resulting trifluoroacetyl chloride was condensed in cold traps cooled to −78° C. After completion of trifluoroacetic anhydride addition, the reaction solution was warmed to 40° C. for one hour to expel dissolved trifluoroacetyl chloride. The yield of trifluoroacetyl chloride condensed in was 27.95 g (92.5% of theoretical). A chloride determination gave a residual chlorine content of 626.2 mg of chloride (17.66 mmole) in the reaction solution. This corresponds to a conversion yield of greater than 99%.

The reaction residue contained pyridinium trifluoroacetate as well as some trifluoroacetic acid, which was removed by spray drying. To prepare larger amounts the example was repeated several times.

EXAMPLE 2

Preparation of trifluoroacetyl chloride and piperidinium trifluoroacetate by reaction of piperidinium hydrochloride with trifluoroacetic anhydride.

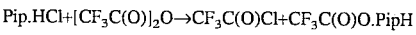

Pip.HCl+[CF$_3$C(O)]$_2$O→CF$_3$C(O)Cl+CF$_3$C(O)O.PipH

With exclusion of moisture (N$_2$ atmosphere), 27.26 g (0.226 mole) of piperidinium hydrochloride were taken up in 25 ml of trifluoroacetic acid and 61.84 g (0.227 mole) of trifluoroacetic anhydride were added continuously dropwise with stirring within one hour at room temperature. Immediately after the addition of a few drops of trifluoroacetic anhydride, vigorous evolution of gas was observed in the reaction flask. The resulting trifluoroacetyl chloride was condensed in cold traps cooled to −78° C. After completion of trifluoroacetic anhydride addition, the reaction solution was warmed to 40° C. for one hour to expel dissolved trifluoroacetyl chloride. The yield of trifluoroacetyl chloride condensed in was 26.97 g (89.9 % of theoretical). A chloride determination gave a residual chlorine content of 778.8 mg of chloride (21.97 mmole) in the reaction solution. This corresponds to a conversion yield of 99.8%.

EXAMPLE 3

Preparation of trifluoroacetyl chloride and benzyltriethylammonium trifluoroacetate by reaction of benzyltriethylammonium hydrochloride with trifluoroacetic anhydride.

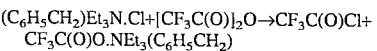

(C$_6$H$_5$CH$_2$)Et$_3$N.Cl+[CF$_3$C(O)]$_2$O→CF$_3$C(O)Cl+ CF$_3$C(O)O.NEt$_3$(C$_6$H$_5$CH$_2$)

With exclusion of moisture (N$_2$ atmosphere), 43.55 g (0.191 mole) of benzyltriethylammonium hydrochloride were taken up with 21 ml of trifluoroacetic acid and 52.20 g (0.249 mole) of trifluoroacetic anhydride were added continuously dropwise with stirring within one hour at room temperature. Immediately after the addition of a few drops of trifluoroacetic anhydride, vigorous evolution of gas was observed in the reaction flask. The resulting trifluoroacetyl chloride was condensed in cold traps cooled to −78° C. After completion of trifluoroacetic anhydride addition, the reaction solution was warmed to 40° C. for one hour to expel dissolved trifluoroacetyl chloride.

The yield of condensed trifluoroacetyl chloride was 20.26 g (80.1% of theoretical). A chloride determination gave a residual chlorine content of 15.3 mg (0.432 mmole) of chloride in the reaction solution. This corresponds to a conversion yield of 87.1%.

EXAMPLE 4

Preparation of trifluoroacetyl chloride and triethylammonium trifluoroacetate by reaction of triethylammonium hydrochloride with trifluoroacetic anhydride.

Et$_3$N.HCl+[CF$_3$C(O)]$_2$O→CF$_3$C(O)Cl+CF$_3$C(O)O.NHEt$_3$

With exclusion of moisture (N$_2$ atmosphere), 31,11 g (0.226 mole) of triethylammonium hydrochloride were taken up in 25 ml of trifluoroacetic acid and 61.84 g (0.294 mole) of trifluoroacetic anhydride were added continuously dropwise with stirring within one hour at room temperature. Immediately after addition of a few drops of trifluoroacetic anhydride, vigorous evolution of gas was observed in the reaction flask. The resulting trifluoroacetyl chloride was condensed in cold traps cooled to −78° C. After completion of trifluoroacetic anhydride addition, the reaction solution was warmed to 40° C. for one hour to expel dissolved trifluoroacetyl chloride. The yield of trifluoroacetyl chloride condensed in was 19.82 g (66.1% of theoretical). A chloride determination gave a residual chlorine content of 1.16 g of chloride (32.7 mmole) in the reaction solution. This corresponds to a conversion yield of 77.4%.

EXAMPLE 5

Preparation of trifluoroacetyl bromide and pyridinium trifluoroacetate by reaction of pyridinium hydrobromide with trifluoroacetic anhydride.

Py.HBr+[CF$_3$C(O)]$_2$O→CF$_3$C(O)Br+CF$_3$C(O)O.PyH

With exclusion of moisture (N$_2$ atmosphere), 36.16 g (0.226 mole) of pyridinium hydrobromide were taken up in 25 ml of trifluoroacetic acid and 61.84 g (0.294 mole) of trifluoroacetic anhydride were added continuously dropwise with stirring within one hour at room temperature. Immediately after addition of a few drops of trifluoroacetic anhydride, vigorous evolution of gas was observed in the reaction flask. The resulting trifluoroacetyl bromide was condensed in cold traps cooled to −78° C. After completion of trifluoroacetic anhydride addition, the reaction solution was warmed to 40° C. for one hour to expel dissolved trifluoroacetyl bromide. The yield of trifluoroacetyl bromide condensed in was 28.18 g (70.5 of theoretical). A bromide determination gave a residual bromine content of 4.90 g of bromide (61.3 mmole) in the reaction solution. This corresponds to a conversion yield of 96.7%.

EXAMPLE 6

Preparation of trifluoroacetyl chloride and sodium trifluoroacetate by reaction of sodium chloride with trifluoroacetic anhydride in the presence of crown ethers.

NaCl+[CF$_3$C(O)]$_2$O→CF$_3$C(O)Cl+CF$_3$C(O)O.Na

With exclusion of moisture, 13.25 g (0.226 mole) of NaCl and 1.03 g (0.004 mole) of 18-crown-6 were taken up in 25 ml of trifluoroacetic acid and 32 ml (0.227 mole) of trifluoroacetic anhydride were added dropwise with stirring at room temperature. The resulting trifluoroacetyl chloride was condensed in cold traps cooled to −78° C. After completion of trifluoroacetic anhydride addition, stirring was continued at room temperature for about 42 hours. The yield of trifluoroacetyl chloride condensed in the cold traps was 28.29 g (55.90% of theoretical). A chloride determination gave a residual chlorine content of 2.95 g of chloride (83.2 mmole) in the reaction solution. This corresponds to a conversion yield of 63.3%.

EXAMPLE 7

Preparation of trifluoroacetyl iodide and sodium trifluoroacetate by reaction of sodium iodide with trifluoroacetic anhydride.

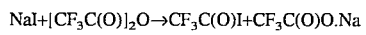

NaI+[CF$_3$C(O)]$_2$O→CF$_3$C(O)I+CF$_3$C(O)O.Na

With exclusion of moisture, 34 g (0.227 mole) of sodium iodide and 1.03 g (0.004 mole) of 18-crown-6 were taken up in 25 ml of trifluoroacetic acid and 32 ml (0.227 mole) of trifluoroacetic anhydride were added dropwise with stirring at room temperature. The solution in the reaction flask solidified immediately after the addition of trifluoroacetic anhydride. Therefore, a further 25 ml of trifluoroacetic acid were added. The resulting acetyl iodide was condensed in cold traps cooled to −78° C. After completion of trifluoroacetic anhydride addition, stirring was continued for about 16 hours at room temperature. The next day, the reaction flask was placed in a water bath containing water at 50° C. for about 8 hours, during which time the temperature in the reaction flask rose to 40° C. The yield of trifluoroacetyl iodide was 17.23 g (33,90 of theoretical). An iodide determination gave a residual iodide content of 11.17 g of iodide (75.5 mmole) in the reaction solution. This corresponds to a conversion yield of 50.5%.

EXAMPLE 8

Preparation of trifluoroacetyl iodide and potassium trifluoroacetate by reaction of potassium iodide with trifluoroacetic anhydride.

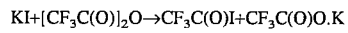

KI+[CF$_3$C(O)]$_2$O→CF$_3$C(O)I+CF$_3$C(O)O.K

With exclusion of moisture, 37.48 g (0.226 mole) of potassium iodide and 0.99 g (0.004 mole) of crown ether were taken up in 25 ml of trifluoroacetic acid, and 32 ml (0.227 mole) of trifluoroacetic anhydride were added dropwise with stirring at room temperature. The resulting trifluoroacetyl iodide was condensed in cold traps cooled to −78° C. After completion of trifluoroacetic anhydride addition, stirring was continued for about 12 hours at room temperature. The next day, the reaction flask was placed in a water bath containing water at 40° C. for about 10 hours. The yield of trifluoroacetyl iodide was 20.06 g (39.64 of theoretical). An iodide determination gave a residual iodide content of 2.60 g of iodide (21.0 mmole) in the reaction solution. This corresponds to a conversion yield of 43.9%.

EXAMPLE 9

Preparation of acetyl chloride and pyridinium acetate by reaction of acetic anhydride with pyridinium chloride.

With exclusion of moisture, 45.33 g (0.392 mole) of pyridinium hydrochloride were taken up in 30 ml of acetic acid in a Claisen apparatus and combined with 36 ml (0.381 mole) of acetic anhydride with stirring at room temperature. Subsequently the temperature was raised to 100° C. in an oil bath, and the temperature was raised slowly to 170° C. over the course of 7 hours. The resulting acetyl chloride was collected in a receiver cooled to 10° C., along with anhydride and acetic acid which also distilled over. The isolated yield of acetyl chloride in the receiver after this reaction period was 7.1% of theoretical. The conversion was about 10%.

In Examples 6 to 8, 18-crown-6 was used. The reactions described in the examples also proceed without addition of crown ethers, but the rate of reaction is reduced.

EXAMPLE 10

Preparation of trifluoroacetyl chloride and aluminum trifluoroacetate by reaction of aluminum trichloride with trifluoroacetic anhydride.

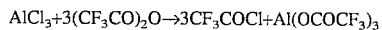

With exclusion of moisture ($N_2$ atmosphere), 39.2 g (0.294 mole) of $AlCl_3$ were taken up in 147 ml of 1,4-dioxane and on three consecutive days a total of 185.25 g (0.882 mole) of trifluoroacetic anhydride (one equivalent $(CF_3CO)_2O$ relative to $AlCl_3$ per day), were added continuously dropwise with stirring within one hour at room temperature. Immediately after addition of a few drops of trifluoroacetic anhydride, evolution of gas was observed in the reaction flask. The resulting trifluoroacetyl chloride was condensed in cold traps cooled to −78° C. After completion of the trifluoroacetic anhydride addition, the reaction solution was heated to 40° C. for two hours to expel dissolved trifluoroacetyl chloride. The total isolated yield of condensed trifluoroacetyl chloride over all three days was 111.72 g, which corresponds to 95.9% of theoretical.

EXAMPLE 11

Preparation of trifluoroethyl trifluoroacetate by reacting trifluoroacetyl chloride with 2,2,2-trifluoroethanol in the presence of pyridinium trifluoroacetate.

30 g (0.16 mole) of the pyridinium trifluoroacetate obtained from Example 1 were taken up in 335 g (3.55 mole) of 2,2,2-trifluoroethanol and circulated in a laboratory scale circulation apparatus (1 liter four-necked flask fitted with precision glass stirrer, prominent pump, 30 cm column packed with Raschig rings) at an internal temperature of 54° C. Subsequently, 134 g (1.01 mole) of trifluoroacetyl chloride, obtained in an analogous manner to Example 1, were metered into the flask via an immersion tube over 100 min. After completion of the trifluoroacetyl chloride addition, the reaction was allowed to continue for 10 minutes. Subsequently the reaction mixture was subjected to fractional distillation via a Vigreux column (distillation temperature 54° C. to 56° C.) to give 177.8 g of trifluoroacetyl trifluoroacetate, corresponding to a yield of 89.8% of the theoretical. The trifluoroethanol/pyridinium salt mixture remaining in the receiving flask can be used again for esterification with the same effectiveness.

EXAMPLES 12–17

Preparation of trifluoroacetic acid esters by reaction of trifluoroacetyl chloride with methanol, ethanol, isopropanol, 4-nitrophenol, pentafluorophenol and allyl alcohol in the presence of pyridinium trifluoroacetate.

In an analogous manner to Example 11, the corresponding esters of trifluoroacetyl chloride with methanol (94%), ethanol (96%), isopropanol (89%), 4-nitrophenol (85%), pentafluorophenol (92%) and allyl alcohol (81%) were also prepared.

EXAMPLE 18

Preparation of 1,1,1-trifluoroethyl trifluoroacetate in the presence of piperidinium trifluoroacetate.

In an analogous manner to Example 2, starting from trifluoroacetic anhydride and piperidinium chloride, trifluoroacetyl chloride and piperidinium trifluoroacetate were prepared and isolated. Then 1,1,1-trifluoroethyl trifluoroacetate was prepared in an analogous manner to Example 11.

EXAMPLE 19

Preparation of trifluoroethyl trifluoroacetate by reaction of trifluoroacetic anhydride with 2,2,2-trifluoroethanol in the presence of pyridinium hydrochloride ("in situ" method).

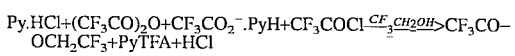

23.11 g (0.2 mole) of pyridinium hydrochloride and 20.0 g (0.2 mole) of 2,2,2-trifluoroethanol were placed in a 250 ml three-necked flask with a precision glass stirrer, dry ice condenser and dropping funnel. Subsequently, 42.01 g (0.2 mole) of trifluoroacetic anhydride were added dropwise over 3 hours at an internal reaction temperature of 52° C. to 55° C. The yield of trifluoroethyl trifluoroacetate was 98% (GC).

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A process for simultaneously preparing a carboxylic acid halide and a carboxylate salt formed from a carboxylate anion and 1/n "onium" cations of nitrogen $M^{n+}$, wherein n+ represents the positive charge of the cation, said process comprising reacting a carboxylic anhydride with a compound corresponding to the formula $M^{n+}(Hal^-)_n$, wherein $Hal^-$ represents chloride, bromide or iodide.

2. A process according to claim 1, wherein said compound corresponding to the formula $M^{n+}(Hal^-)_n$ is an anhydrous waste product.

3. A process according to claim 3, wherein said anhydrous waste product is a spent catalyst material containing $M^{n+}(Hal^-)_n$.

4. A process according to claim 1, wherein said carboxylic anhydride is an anhydride of a carboxylic acid which contains from 2 to 4 carbon atoms.

5. A process according to claim 1, wherein said carboxylic anhydride is an anhydride of a carboxylic acid containing from 2 to 4 carbon atoms substituted with from 1 to 17 halogen atoms.

6. A process according to claim 6, wherein said carboxylic anhydride is an anhydride of a carboxylic acid containing from 2 to 4 carbon atoms substituted with from 1 to 7 fluorine atoms.

7. A process according to claim 1, wherein $M^{n+}$ represents an "onium" cation of nitrogen corresponding to the formula $R^1R^2R^3R^4N^+$, wherein $R^1$, $R^2$, $R^3$ and $R^4$ are independently selected from the group consisting of hydrogen, alkyl containing from 1 to 20 carbon atoms, aryl and aralkyl, or wherein the nitrogen atom and at least two of $R^1$, $R^2$, $R^3$ and $R^4$ form a saturated or unsaturated ring system.

8. A process according to claim 7, wherein $M^{n+}$ represents piperidinium, pyridinium or $R^{1'}R^{2'}R^{3'}R^{4'}N^+$, in which $R^{1'}$, $R^{2'}$, $R^{3'}$ and $R^{4'}$ are independently selected from hydrogen, alkyl containing from 1 to 15 carbon atoms and benzyl.

9. A process according to claim 1, wherein $Hal^-$ represents chloride.

10. A process according to claim 1, wherein a reaction mixture containing carboxylic acid halide and carboxylate salt is obtained in said reacting step, further comprising using said reaction mixture in an acylation process.

11. A process according to claim 1, wherein said reacting step produces a mixture of carboxylic acid halide and carboxylate salt, further comprising separating the carboxylic acid halide and carboxylate salt.

12. A process according to claim 11, further comprising using the separated carboxylic acid halide or carboxylate salt as an acylating or alkylating reagent, whereby $M^{n+}(Hal^-)_n$ is formed, and reacting the formed $M^{n+}(Hal^-)_n$ with a carboxylic anhydride to prepare more carboxylic acid chloride and carboxylate salt.

13. A process according to claim 1, wherein said reacting step produces a mixture of carboxylic acid halide and carboxylate salt, further comprising reacting said mixture with an alcohol to form a carboxylic acid ester.

14. A process according to claim 13, wherein the step of reacting said mixture with an alcohol is performed simultaneously with the preparation of said mixture.

15. A process according to claim 13, wherein the step of reacting said mixture with an alcohol is performed subsequent to the preparation of the mixture.

16. A process for simultaneously preparing a carboxylic acid halide and a carboxylate salt formed from a carboxylate anion and 1/n cations $M^{n+}$, wherein $M^{n+}$ is a metal cation from Group I, Group II or Group III of the periodic table and n+ represents the positive charge of the cation, said process comprising reacting a carboxylic anhydride containing from 2 to 4 carbon atoms substituted with from 1 to 7 halogen atoms with a compound corresponding to the formula $M^{n+}(Hal^-)_n$, wherein $Hal^-$ represents chloride or bromide.

17. A process according to claim 16, wherein said compound corresponding to the formula $M^{n+}(Hal^-)_n$ is an anhydrous waste product.

18. A process according to claim 17, wherein said anhydrous waste product is a spent catalyst material containing $M^{n+}(Hal^-)_n$.

19. A process according to claim 16, wherein said carboxylic anhydride is substituted with from 1 to 7 fluorine atoms.

20. A process according to claim 16, wherein $M^{n+}$ represents $Na^+$, $K^+$ or $Al^{3+}$.

21. A process according to claim 16, wherein $Hal^-$ represents chloride.

22. A process according to claim 16, wherein a reaction mixture containing carboxylic acid halide and carboxylate salt is obtained in said reacting step, further comprising using said reaction mixture in an acylation process.

23. A process according to claim 16, wherein said reacting step produces a mixture of carboxylic acid halide and carboxylate salt, further comprising separating the carboxylic acid halide and carboxylate salt.

24. A process according to claim 23, further comprising using the separated carboxylic acid halide or carboxylate salt as an acylating or alkylating reagent, whereby $M^{n+}(Hal^-)_n$ is formed, and reacting the formed $M^{n+}(Hal^-)_n$ with a carboxylic anhydride to prepare more carboxylic acid chloride and carboxylate salt.

25. A process according to claim 16, wherein said reacting step produces a mixture of carboxylic acid halide and carboxylate salt, further comprising reacting said mixture with an alcohol to form a carboxylic acid ester.

26. A process according to claim 25, wherein the step of reacting said mixture with an alcohol is performed simultaneously with the preparation of said mixture.

27. A process according to claim 25, wherein the step of reacting said mixture with an alcohol is performed subsequent to the preparation of the mixture.

* * * * *